United States Patent
Croizat et al.

(10) Patent No.: US 9,833,362 B2
(45) Date of Patent: *Dec. 5, 2017

(54) BANDAGE SET FOR TREATING WOUND CAVITIES

(71) Applicant: Paul Hartmann AG, Heidenheim (DE)

(72) Inventors: Pierre Croizat, Herbrechtingen (DE); Axel Eckstein, Heidenheim (DE); Cornelia Wolf, Herbrechtingen (DE); Njikoha Ebigbo, Neu-Ulm (DE)

(73) Assignee: Paul Hartmann AG, Heidenheim (DE)

( * ) Notice: Subject to any disclaimer, the term of this patent is extended or adjusted under 35 U.S.C. 154(b) by 771 days.

This patent is subject to a terminal disclaimer.

(21) Appl. No.: 14/176,699

(22) Filed: Feb. 10, 2014

(65) Prior Publication Data

US 2014/0228788 A1 Aug. 14, 2014

Related U.S. Application Data

(60) Provisional application No. 61/765,191, filed on Feb. 15, 2013.

(30) Foreign Application Priority Data

Feb. 13, 2013 (DE) .................. 10 2013 002 497

(51) Int. Cl.
- *A61F 13/02* (2006.01)
- *A61F 17/00* (2006.01)
- *A61F 13/00* (2006.01)

(52) U.S. Cl.
CPC .... *A61F 13/0216* (2013.01); *A61F 13/00021* (2013.01); *A61F 13/00068* (2013.01); *A61F 17/00* (2013.01)

(58) Field of Classification Search
CPC combination set(s) only.
See application file for complete search history.

(56) References Cited

U.S. PATENT DOCUMENTS

| | | |
|---|---|---|
| 7,922,703 B2 | 4/2011 | Riesinger |
| 8,030,534 B2 | 10/2011 | Radl et al. |

(Continued)

FOREIGN PATENT DOCUMENTS

| | | |
|---|---|---|
| DE | 202004018245 U1 | 7/2005 |
| DE | 102006031418 A1 | 1/2007 |

(Continued)

OTHER PUBLICATIONS

International Preliminary Report on Patentability and Written Opinion dated Aug. 27, 2015 for International Application No. PCT/EP2014/052734.

*Primary Examiner* — Todd J Scherbel
*Assistant Examiner* — Guy K Townsend
(74) *Attorney, Agent, or Firm* — Dilworth & Barrese, LLP

(57) ABSTRACT

The invention relates to a bandage set suitable for use in the treatment of wound cavities, especially for use in the treatment of wound cavities by means of negative pressure, comprising i) a first bandage material as wound contact layer, comprising a flexible, perforated film (11, 21, 31) having a first and a second side, the perforations (15) present in the film being provided in such a way that the perforation edges (16) protrude from the second side of the film (11, 21, 31), with three-dimensional structures being present on the second side of the film (11, 21, 31), and the first side being intended for contacting with a wound base (3), more particularly the internal surface of a wound tube, ii) a separately provided second bandage material for introduction into a wound cavity, comprising a porous polymer foam (12, 22, 32), the polymer foam (12, 22, 32) being an open-cell polymer foam which comprises struts (14) on or (Continued)

close to its surface and/or which comprises, on its surface, hollow spaces (13) open toward the surface, and the struts (14) and/or hollow spaces (13) forming three-dimensional structures, characterized in that the first bandage material has a surface area sufficient to envelop at least 75% of the surface of the second bandage material, and the structures present on the second side of the first bandage material can form an adhesive connection with the structures present on the surface of the second bandage material, the second side of the film (11, 21, 31) being intended for partial or complete envelopment of the surface of the polymer foam (12, 22, 32) immediately before the wound treatment, and so, after introduction of the composite composed of first and second bandage material into a wound cavity, movement of the first bandage material with respect to the second bandage material can be avoided as far as possible during the therapy and/or simultaneous removal of the first bandage material and the second bandage material is facilitated owing to the adhesive connection between the first bandage material and the second bandage material.

16 Claims, 3 Drawing Sheets

(56) References Cited

U.S. PATENT DOCUMENTS

| | | | |
|---|---|---|---|
| 8,551,075 B2 * | 10/2013 | Bengtson | A61M 1/008 604/541 |
| 8,603,053 B2 | 12/2013 | Riesinger | |
| 2004/0209041 A1 | 10/2004 | Muth et al. | |
| 2007/0141128 A1 * | 6/2007 | Blott | A61M 1/0058 424/445 |
| 2008/0243044 A1 * | 10/2008 | Hunt | A61M 1/0088 602/58 |
| 2009/0093779 A1 | 4/2009 | Riesinger | |
| 2009/0099519 A1 * | 4/2009 | Kaplan | A61F 7/12 604/113 |
| 2009/0318842 A1 * | 12/2009 | Kairinos | A61F 13/0226 602/52 |
| 2010/0106115 A1 * | 4/2010 | Hardman | A61M 1/0088 604/319 |
| 2010/0185163 A1 | 7/2010 | Heagle | |
| 2011/0112492 A1 * | 5/2011 | Bharti | A61M 1/0088 604/319 |
| 2011/0152800 A1 * | 6/2011 | Eckstein | A61M 1/0088 604/319 |
| 2011/0172617 A1 | 7/2011 | Riesinger | |
| 2011/0224630 A1 * | 9/2011 | Simmons | A61M 1/0088 604/317 |
| 2011/0251567 A1 * | 10/2011 | Blott | A61M 1/0058 604/290 |
| 2011/0270301 A1 * | 11/2011 | Cornet | A61B 17/085 606/213 |
| 2012/0136326 A1 * | 5/2012 | Croizat | A61F 13/00017 604/319 |
| 2012/0157945 A1 | 6/2012 | Robinson et al. | |
| 2013/0123723 A1 | 5/2013 | Tout et al. | |
| 2014/0228787 A1 * | 8/2014 | Croizat | A61F 13/00029 604/319 |

FOREIGN PATENT DOCUMENTS

| | | |
|---|---|---|
| DE | 202006016821 U1 | 3/2007 |
| DE | 102006017194 A1 | 10/2007 |
| DE | 102008061536 A1 | 6/2010 |
| EP | 2537494 A1 | 12/2012 |
| EP | 2545946 A2 | 1/2013 |
| WO | 1996/014038 A1 | 5/1996 |

* cited by examiner

BANDAGE SET FOR TREATING WOUND CAVITIES

CROSS REFERENCE TO RELATED APPLICATIONS

The present application claims priority to U.S. Provisional application No. 61/765,191 filed Feb. 15, 2013 and to German Application DE 10 2013 002 497.8 filed Feb. 13, 2013, both of which are incorporated by reference herein.

DESCRIPTION

The present invention relates to a bandage set for use in the treatment of wound cavities, especially by means of negative pressure, comprising a first bandage material as wound contact layer and a separately provided second bandage material as wound filler.

Apparatuses for the negative-pressure therapy of wounds and bandages as part of such apparatuses are known in the prior art. For example, WO1993/009727 describes an apparatus for promoting wound healing through the application of negative pressure to the skin region comprising the wound and surrounding the wound.

During the negative-pressure therapy of wounds, a negative-pressure-generating device communicates via a suction line with the wound or the wound space, where an airtight and negative-pressure-tight wound bandage is provided for airtight and negative-pressure-tight closure of the wound and the wound space, making it possible to establish negative pressure in the wound space and to aspirate fluids from the wound space into a container typically arranged between the negative-pressure-generating device and the wound. In this connection, the expression "negative pressure" refers to air pressure which is reduced within the wound bandage with respect to the ambient air pressure (atmospheric air pressure). "Within the wound bandage" is understood to mean the gap (wound space) formed by the airtight covering material and the body tissue in the wound region. "Negative pressure" is frequently also referred to as "reduced pressure". In the context of the invention, the pressure difference between the air pressure within the wound bandage and the ambient air pressure is specified in mmHg (millimeters of mercury), since this is conventional in the field of negative-pressure therapy. 1 mmHg corresponds to one Torr or 133.322 Pa (pascal). In the context of the invention, the negative pressure, i.e. the pressure difference between the air pressure within the wound bandage and the ambient air pressure, is specified as a positive numerical value in mmHg.

Negative-pressure therapy can be used to treat a multiplicity of different wound types, for example pressure sores (decubitus ulcers), ulcers, burns or wounds resulting from trauma. More particularly, negative-pressure therapy is used in the treatment of poorly healing and/or infected wounds.

Wounds having complex wound geometry can comprise wound cavities. In the context of the present invention, the expression "wound cavity" is understood to mean a wound region having a subdermal extension, for example a wound pocket or wound tube, it being possible for the wound tube to be blind-ending or continuous (wound tunnel). In English terminology, wound cavities are also referred to as "wound sinus" or "sinus tract".

Wound regions having a subdermal extension can be attributed to a multiplicity of very different causes. The occurrence of a wound cavity can, for example, be associated with an inflammatory process. Inflammatory processes are typically involved in the pathogenesis of chronic or delayed-healing wounds. The inflammation process can lead to necrotic degradation of tissue and thus to the formation of hollow spaces in the wound region. Similarly, local infections, which occur for example as a result of implantation of medical devices and prostheses, can contribute to inflammation and subsequently to the formation of deep wound pockets. Wound cavities can also occur as a result of traumatic injuries, for example owing to degloving, contusion, avulsion or ballistic trauma. Owing to the microorganisms introduced during the accident, there is additionally a high risk of infection, which brings along the risk of additional, inflammation-related tissue loss.

To explore a wound cavity, probing of the hollow spaces is frequently required. Treating a wound comprising one or more wound cavities can comprise tamponading the wound hollow with foams, gauze products or alginates. In the case of high production of exudate, the fluid is discharged from the wound via drainages. Lining the wound bed with filling materials prevents drying-up of the wound bed and supports the formation of functional granulation tissue. Furthermore, the aim is to prevent the formation of undesired granulation bridges, since they can lead to the formation of encapsulated hollow spaces. Difficulties frequently arise during removal of the materials used as tamponade.

Negative-pressure therapy represents a new treatment option for treating wounds having complex wound geometry. To this end, a foam material can be introduced into the cavity and the wound space can be connected to a negative-pressure source in order to promote the formation of granulation tissue and to discharge wound exudate. The foam is gradually shortened over successive treatment cycles. However, in the case of this treatment method, there is the risk, especially when treating deep, narrow wound hollows, of foam remnants remaining during bandage change. In addition, it has become apparent that the foam material can collapse under the influence of negative pressure, preventing the discharge of wound exudate from the wound pockets (secretion accumulation). To avoid secretion accumulation, it has been proposed to introduce drainage lines (Redon's suction drainage) into extended wound hollows, making it possible to drain the wound exudate without impediment. At the same time, the central open region of the wound, into which the cavities discharge, is lined with a foam. The drainage lines are laid from the negative-pressure connecting piece, through the foam in the central open region of the wound, to the wound hollows, making it possible for the cavities to be kept open and liquid contained therein to be aspirated (Grimm, Loos and Horch in Zentralbl Chir 2006; 131: pp. 19-23). However, when the wound base, i.e. the walls of the cavity, is pressed against the drainage line during the application of negative pressure, this can lead to obstruction of the openings of the drainage line.

WO2004/018020 describes a flexible wound insert for negative-pressure therapy, which insert can be introduced into wound tubes or undermined regions. The planar wound insert, which if necessary can be rolled up to form a conducting element, has a multiplicity of openings and, optionally, channels. By introducing the wound insert into a wound cavity, the aim is to avoid premature wound closure and/or the encapsulation of hollow spaces as a result of the formation of granulation bridges.

Arising from medical practice is the requirement of providing an improved wound dressing for wound cavities. A wound dressing of this type should line the cavity as completely as possible, but without adhesively bonding to or growing together with the wound base. One requirement which has been found to be of crucial importance is that, during bandage change, no material remnants at all must remain in the poorly accessible hollow spaces of the wound. Remaining material pieces can lead to severe complications after the treatment, for example the formation of abscesses. Furthermore, the aim of the wound dressing is to fully ensure, without impediment, exudate drainage even during the negative-pressure therapy. Altogether, it should be possible to use the wound dressing flexibly and for the user to tailor the wound dressing to the particular wound situation. Furthermore, the wound dressing should be simple to apply and be removable in as few work steps as possible.

The present invention proposes, for the treatment of wounds comprising wound cavities, a bandage set and also a composite comprising at least two components, obtainable using the bandage set.

According to the invention, the bandage set, which is suitable in particular, but not exclusively, for use in the treatment of wound cavities by means of negative pressure, comprises a first bandage material as wound contact layer. The wound contact layer comprises a flexible, perforated film having a first and a second side. The perforations present in the film are provided in such a way or are introduced into the film in such a way that the perforation edges protrude from the second side of the film. The perforation edges protruding from the second side of the film thus form three-dimensional structures present on the second side of the film. The first side of the film is intended for contacting with a wound base, more particularly for contacting with the internal surface of a wound tube. The bandage set further comprises a separately provided second bandage material for introduction into a wound tube, which material is thus intended as wound filler. The second bandage material comprises a porous polymer foam, the polymer foam being an open-cell polymer foam which comprises struts on or close to its surface and/or which comprises, on its surface, hollow spaces open toward the surface. Here, the struts and/or hollow spaces form three-dimensional structures. According to the invention, it is necessary for the first bandage material to have a surface area sufficient to envelop at least 75%, preferably at least 85%, in particular at least 95%, of the surface of the second bandage material. According to the invention, it is further necessary for the structures present on the second side of the first bandage material to be able to form an adhesive connection with the structures present on the surface of the second bandage material. The second side of the film is intended for partial or complete envelopment of the surface of the polymer foam immediately before placement of the wound dressing or immediately before the wound treatment, and so a composite composed of first bandage material and second bandage material is produced. The composite is thus prepared by the user immediately before the wound treatment, the user being able to tailor the size and shape of the components to the wound proportions by cutting to size. After introduction of the composite composed of first and second bandage material into a wound cavity, movement of the first bandage material with respect to the second bandage material can be avoided as far as possible during the therapy and/or simultaneous removal of the first bandage material and the second bandage material can be facilitated owing to the adhesive connection between the first bandage material and the second bandage material.

The composite which is proposed by the invention and which comprises at least two components is likewise intended and suitable for use in the treatment of wound cavities, especially for use in the treatment of wound cavities by means of negative pressure. With the composite according to the invention, the user, i.e. typically the physician performing the treatment, is provided with a wound dressing specifically tailored for treating wound cavities. The composite comprises a first bandage material as wound contact layer. Here, the first bandage material comprises a flexible, perforated film having a first and a second side, the perforations present in the film being provided in such a way that the perforation edges protrude from the second side of the film, with three-dimensional structures being present on the second side of the film. The first side is intended for contacting with a wound base, more particularly the internal surface of a wound tube. The composite further comprises a second bandage material for introduction into a wound cavity. The second bandage material comprises a porous polymer foam, the polymer foam being an open-cell polymer foam which comprises struts on or close to its surface and/or which comprises, on its surface, hollow spaces open toward the surface, and the struts and/or hollow spaces forming three-dimensional structures. It is essential that the structures present on the second side of the first bandage material can form an adhesive connection with the structures present on the surface of the second bandage material. Furthermore, the film must be present on at least 75%, preferably at least 85%, in particular at least 95%, of the surface of the polymer foam. The film thus forms an envelopment of the polymer foam, the film, with its second side, being in contact with the polymer foam. The result of this is that, after introduction of the composite composed of first and second bandage material into a wound cavity, movement of the first bandage material with respect to the second bandage material can be avoided as far as possible during the therapy and/or simultaneous removal of the first bandage material and the second bandage material is facilitated owing to the adhesive connection between the first bandage material and the second bandage material.

The composite composed of first and second bandage material (hereinafter also referred to as "wound dressing") can be used in combination with bandage components known per se from the prior art. More particularly, the wound dressing is suitable for use in combination with components normally usable for negative-pressure wound therapy, for example a further porous wound filler, an airtight self-adhesive covering film, a negative-pressure connecting means, a secretion container and a negative-pressure source.

The composite according to the invention allows improved treatment of wounds having wound cavities, especially when using negative-pressure therapy. The new type of wound dressing therefore allows in particular improved treatment of wounds comprising wound cavities by means of negative pressure, with wound healing being supported, the treatment being facilitated and the patient being protected from undesired complications. The improvements and advantages achievable using the wound dressing compared to the prior art thus concern the positive healing process of the negative-pressure therapy, the manageability of the wound dressing for the physician performing the treatment and also the avoidance of adverse effects from the negative-pressure therapy.

A substantial improvement in the treatment of wounds comprising regions with cavities is that the wound dressing according to the invention can be tailored to the specific wound situation by the user, for example the physician performing the treatment, immediately before the wound treatment. Because of tailoring of the composite to the dimensions of the wound cavity to be treated, the cavity can be completely filled by the wound dressing, without any hollow spaces remaining, in which wound exudate can be collected. Furthermore, during the treatment, the wound contact layer is continuously in contact with the wound base formed by the walls of the cavity. Very extensive coverage of the wound base during the presence of negative pressure can promote the formation of granulation tissue.

In practice, the composite which is held together by adhesive forces and introduced into the wound cavity and which is composed of a perforated film which has three-dimensional structures with a porous polymer foam has been found to be particularly advantageous in various respects.

Firstly, the three-dimensional perforations present in the film can form a capillary effect, which can bring about effective draining of the wound exudate of the wound base through the film toward the foam. The open-cell polymer foam in turn ensures, across its internal hollow spaces, unimpeded further transport of the fluid toward the wound opening. With respect to the dimensions of the perforations, an open diameter of preferably at least 100 µm and not more than 1000 µm, particularly preferably at least 300 µm and not more than 500 µm, has been found to be advantageous, since, in the case of such dimensioning, firstly, a sufficient capillary effect is present and, secondly, sufficient permeability through the inherently fluid-impermeable film is ensured. In this connection, the height of the three-dimensional structures (maximum extent of the three-dimensional structure from the plane of the film up to the perforation edges) should, in connection with the capillary effect, preferably be from 100 µm to 2000 µm, particularly preferably from 300 µm to 700 µm.

Secondly, envelopment of the foam with a film results in stabilization of the polymer foam in narrow wound tubes, making it possible to largely avoid collapse of the foam in the presence of negative pressure. This effect contributes to the wound exudate being drained even from narrow cavities over the entire period of the therapy.

In addition, the film having a largely smooth surface on its first side provides an atraumatic wound contact layer which does not show any tendency to grow together with the freshly formed granulation tissue. Furthermore, the composite which is held together by adhesive forces and which is composed of a perforated film with the porous polymer foam can be removed in one step after completion of the therapy.

Lastly, the film enveloping the foam ensures that no foam pieces remain in the cavities, making it possible to avoid as far as possible a substantial complication which frequently occurs during the treatment of cavities. As a result, the safety of negative-pressure treatment of wound cavities can be considerably improved.

According to the invention, the composite composed of a perforated film which has three-dimensional structures with a porous open-cell polymer foam which comprises struts on or close to its surface and/or which comprises, on its surface, hollow spaces open toward the surface, the struts and/or hollow spaces forming three-dimensional structures, is held together by adhesive forces. The adhesive forces required for this purpose ought to be sufficiently strong to hold the composite together during introduction into the cavity, additionally during the period of wound treatment and lastly during pulling out of the wound dressing during bandage change. It is essential to the invention that the composite is held together by sufficiently strong adhesive forces both in the dry state (for example, when applying the wound dressing) and in the wet state (for example, during the therapy or after completion of the therapy).

When selecting suitable materials for the first and the second bandage material, use can be made of the sliding friction force $F_s$, measured in accordance with DIN EN ISO 8235, to estimate the adhesive force present between first and second bandage material. To this end, the sliding friction force $F_s$ occurring between first and second bandage material is determined according to the method described in the exemplary embodiment, which method is based on DIN EN ISO 8235. Preferably, the sliding friction force $F_s$ is determined both in the dry and in the wet state.

In a particularly preferred embodiment of the invention, a static sliding friction force $F_s$, measured in accordance with DIN EN ISO 8235, of at least 3 N is required in order to move the first bandage material in the wet state against the second bandage material in the wet state and/or a static sliding friction force $F_s$ of at least 6 N, measured in accordance with DIN EN ISO 8235, is required in order to move the first bandage material in the dry state against the second bandage material in the dry state. Particularly preferably, a static sliding friction force $F_s$, measured in accordance with DIN EN ISO 8235, of at least 5 N is required in order to move the first bandage material in the wet state against the second bandage material in the wet state and/or a static sliding friction force $F_s$ of at least 8 N, measured in accordance with DIN EN ISO 8235, is required in order to move the first bandage material in the dry state against the second bandage material in the dry state.

Since the sliding friction force present between the surfaces can, for manufacturing reasons, vary in the longitudinal direction ("machine direction", also referred to as "MD") and transverse direction of the materials, an "at least required static sliding friction force $F_s$" is understood here to mean the minimum static sliding friction force $F_s$ occurring in the case of different orientations of the plies to one another. This can ensure that the composite composed of film and polymer foam is held together by sufficiently strong adhesive forces both in the dry state and in the wet state.

The first bandage material comprises a flexible, perforated film having a first and a second side, as wound contact layer.

It is essential that the wound contact layer consists of a material which does not adhesively bond to or grow together with the wound base over the period of use. The material ought therefore to have atraumatic properties. Preferably, the first bandage material comprises a thermoplastic film. Suitable materials for a thermoplastic film comprise, in particular, ethylene-vinyl acetate (EVA), polyurethane (PU), polyethylene (PE), polyethylene terephthalate (PET), polytetrafluoroethylene (PTFE), polyvinyl chloride (PVC), thermoplastic elastomers (TPE), polyorganosiloxane (silicone) or a mixture thereof. In this connection, the name TPE comprises olefin-based thermoplastic elastomers (TPO), crosslinked olefin-based thermoplastic elastomers (TPV), urethane-based thermoplastic elastomers (TPU), thermoplastic polyester elastomers or thermoplastic copolyesters (TPC), styrene block copolymers (TPS) and thermoplastic copolyamides (TPA). Preferably, the thermoplastic film is a PE film.

The basis weight of the film should be at least 30 g/m$^2$ and not more than 150 g/m$^2$, preferably at least 45 g/m$^2$ and not more than 95 g/m$^2$ and in particular at least 55 g/m$^2$ and not more than 65 g/m$^2$.

The flexible film intended as wound contact layer is applied to the second bandage material comprising a polymer foam or wrapped around the second bandage material before application of the wound dressing. The flexible film thus forms an envelope partly or completely covering the second bandage material.

Normally, the wound contact layer is predominantly present on the polymer foam as a single-ply material layer. However, it is also possible to apply to the foam more than one film ply on top of one another. In particular, wrapping the foam with the film frequently results in an at least two-ply region in the overlap region of the film webs. The material thickness of the film is (without taking into account the three-dimensional structures present on the second surface) from 10 to 1000 µm, preferably from 10 to 500 µm.

The second bandage material comprises an open-cell porous polymer foam, more particularly a foam composed of polyurethane, a foam composed of silicone or a foam composed of polyvinyl alcohol. Particularly preferably, the second bandage material comprises a foam composed of polyester polyurethane.

With respect to its external shape, the second bandage material is preferably in the form of a cuboid or in the form of a cylinder. A cylinder having a low diameter (d) compared to its height (h), i.e. a hose-shaped cylinder, is particularly suitable for introduction into a narrow wound tube. Particularly preferably, the second bandage material is present in the form of a hose-shaped cylinder in which the ratio of height (h) to diameter (d) is at least 3, in particular at least 5, very particularly preferably at least 10.

For the user, it can prove to be very practical when the second bandage material is provided to the user in the form of a selection of hose-shaped foam segments (the length of which could, for example, be 10 cm in each case) having different diameters. The diameters could be, for example, 1 cm, 2 cm, 3 cm, 4 cm and 5 cm. After exploring the wound, the user can then select a foam having a diameter suitable for the cavity to be treated.

In a further preferred embodiment, the second bandage material is present in the form of a cuboid having sides a; b; c, more particularly in the form of a cuboid stretched in length and having a ratio of the side lengths of the cross-sectional area formed by sides (a; b) of $0.5<(a:b)<2$, the longer side c being intended to be longer than the diagonal of the side area (a; b). Particularly preferably, the cuboid has an approximately square ratio of the side lengths of $0.9<(a:b)<1.1$, the longer side c being intended to be at least two times, more particularly at least five times, the diagonal of the side area (a; b). This particularly preferred embodiment gives a foam block stretched in length and having a cross section which is approximately (in the case of $0.9<(a:b)<1.1$) or completely (in the case of $a=b$) square.

Analogous to the hose-shaped foam segments described above, it can also prove very practical here for the user when the second bandage material is provided in the form of a selection of foam segments (the length of which could, for example, be 10 cm in each case) having different diameters. The diameters (length of a side a in the case of a square cross section) could, for example, be 1 cm, 2 cm, 3 cm, 4 cm and 5 cm.

In the context of the invention, the second bandage material can also be present in further embodiments not described in more detail here. For medical use, it is advantageous when the manufacturer has already provided the second bandage material with an external shape, which facilitates tailoring to a cavity to be treated.

Tailoring of the second bandage material to a cavity to be treated is normally achieved by cutting to size, for example using a sterilized pair of scissors or using a sterilized scalpel.

The second bandage material can be one-ply or comprise multiple layers. In the case of a second bandage ply comprising multiple layers, it is possible for the layers to be detachably or undetachably joined to one another. Holding together of the layers can, for example, be established by wrapping the plies with a further material and/or with the first bandage ply. In the case of a cylindrical second bandage ply comprising multiple layers, a concentric arrangement of the layers may be favorable. Optionally, the second bandage material can comprise one or more additional layers of a textile material such as a woven or nonwoven, for example a nonwoven fabric composed of synthetic polymers such as polyamide, polyester or polypropylene. For example, it would be conceivable for a cylindrical second bandage material to comprise a shell composed of an open-cell polymer foam and a core composed of a nonwoven.

According to the invention, the second bandage material comprises an open-cell porous polymer foam. A cell is the individual hollow space which is formed during the production of foams and which is partly or completely enclosed by cell walls and/or cell struts. A closed cell is typically a cell which is completely enclosed by its walls and therefore not connected with other cells via the gas phase. An open cell is typically a cell which is connected with other cells via the gas phase. In the context of this application, the term open-cell means that the foam contains at least 60% open cells, preferably at least 90% open cells, more preferably at least 98% open cells, in particular substantially 100% open cells, based on the total number of cells. The proportion of open cells in the foam is typically determined in accordance with ASTM D 2856-87, method B). Cell wall is typically understood to mean the wall enclosing the cell. The cell wall can also be referred to as a cell membrane. Cell strut or strut is typically understood to mean the region of the cell wall which separates more than two cells from one another. The open-cell foam usable in the context of the invention can be a reticulated or nonreticulated foam. A reticulated foam is understood to mean a foam which substantially comprises only struts. In the case of a reticulated foam, the cell walls are therefore substantially removed.

It is essential to the invention that structures present on the second side of the first bandage material can form an adhesive connection with structures present on the surface of the second bandage material. Accordingly, the surface of the second side of the first bandage material and the surface of the second bandage material must contain three-dimensional structures (also referred to as 3D structures) which bring about adhesion between the two surfaces. The adhesion is, in particular, adhesion based on a form fit or a force fit.

The three-dimensional structures present on the second surface of the first bandage material are perforations introduced into the film, the perforation edges protruding from the second side of the film. Here, the 3D structures protrude solely from the second surface, and so the second surface has a rough quality, whereas the first surface, which is intended for contacting with a wound base, has a very extensively smooth quality.

The perforations introduced into the film can, for example, protrude as craters from the plane of the film, forming a microstructure which can form an adhesive connection with a suitable opponent on the surface of the second bandage material.

The three-dimensional structures which allow adhesion and which are present in the open-cell polymer foam are the struts of the foam cells and/or hollow spaces open toward the surface of the foam.

To achieve the desired adhesion effect, care must be taken when selecting the bandage material for producing the second bandage ply that a sufficient proportion of foam struts is present on or close to the foam surface and is thus exposed to access of adhesive microstructures of the first bandage material and/or that a sufficient number of hollow spaces open toward the surface of the foam is present. The struts are substantially present within the foam body, and so they typically do not protrude beyond the plane of the three-dimensionally structured foam surface. A hooking or other adhesion-causing interaction of the three-dimensional structures present on the surface of the first bandage material with the microstructures on the surface of the second bandage material, viz. the perforation edges and the struts of the foam, can only take place when the participating structural elements are coordinated with one another in terms of their dimensions. Alternatively or additionally, i.e. in an adhesion-strengthening manner, an adhesive interaction with the three-dimensional microstructures present on the first bandage material can be achieved by a multiplicity of hollow spaces open toward the first surface of the foam, into which the microstructures present on the second side of the film can penetrate, forming a form-fit and/or force-fit connection. Viewed at the microscopic level, the surface of an open-cell polymer foam comprising a multiplicity of hollow spaces open toward the surface of the foam has a three-dimensional surface structure. The hollow spaces open toward the surface are cells which are present in the interior of the foam and which are partially exposed by cutting of the foam that is required during the production of the bandage ply. To achieve an adhesive interaction between the microstructures present on the film and the hollow spaces present on the foam, it is likewise necessary for the microstructures present on both bandage plies and the hollow spaces open toward the surface of the foam to be coordinated with one another in terms of their dimensions.

As already described, it has been found here to be particularly advantageous when, in particular, a crater-shaped structure is present on the second surface of the film. It is important here that the crater-shaped structure protrudes beyond the planar surface of the film to an extent that allows adhesion. However, the structure should not protrude too far from the surface, since otherwise the strength of the hooking microstructures may lessen. The crater-shaped structure is therefore preferably of a height of at least 100 µm and not more than 2000 µm, in particular of at least 200 µm and not more than 1000 µm and very particularly preferably of at least 300 µm and not more than 700 µm. Height is understood here to mean the maximum extent of the three-dimensional structure that is measured perpendicularly with respect to the plane of the film. The measurement can be done on the basis of suitable micrographs of film cross sections. In addition, the adhesion effect of the microstructures formed by the perforation is affected by the angle formed by the plane of the crater walls against the plane of the planar film. It has been found here that it is possible to observe effective adhesion in particular when said angle is at least 10° and not more than 90°, preferably at least 45° and not more than 80°.

In a particularly advantageous embodiment in the context of the invention, it has been found to be particularly advantageous with respect to adhesion when the first and the second bandage material have the following features in combination:

a) The first bandage material (wound contact layer) comprises a transparent, three-dimensionally perforated film composed of polyethylene. The perforation edges protrude as craters from the second side of the film. The height of the three-dimensional funnel-shaped structure present on the second side is from 300 µm to 700 µm. The thickness of the film material (material thickness without taking the perforations into account) is from 10 µm to 100 µm. The open surface of the perforations present in the film is at least 19% and not more than 23%, preferably at least 20% and not more than 22%, of the surface extent of the film. The number of openings present in the first film per unit area is at least 270 per $cm^2$ and not more than 290 per $cm^2$. The diameter of the perforations, measured in the plane of the film, is at least 250 µm and not more than 350 µm. The basis weight of the film, measured in accordance with EN ISO 2286-2, is at least 55 $g/m^2$ and not more than 65 $g/m^2$.

b) The second bandage material comprises an open-cell polymer foam, obtainable by reacting a mixture comprising the components (i) polyisocyanate, (ii) polyester polyol, (iii) blowing agent, and (iv) catalyst. The elongation at break of the foam, measured in accordance with DIN 53571, is from 280% to 300%. The foam has a cell count (=number of pores along a straight line laid out on the foam surface in the machine direction per cm) of from 8 to 15 per cm. The cell count is preferably determined microscopically. The foam has a bulk density, measured in accordance with DIN EN ISO 845 (test specimen having dimensions of 100 mm×100 mm×50 mm, conditioning for 24 h in a standard atmosphere (23° C., 50% rel. air humidity, 1013 mbar)), of between 25.4 and 26.2 $kg/m^3$ and an air permeability, measured in accordance with DIN EN ISO 9237 (20 mm test thickness, 20 $cm^2$ test area, 200 Pa differential pressure), of from 2620 $l/(m^2\ sec)$ to 2740 $l/(m^2\ sec)$. A foam which is particularly highly suitable in the context of this embodiment is obtainable from a mixture comprising the components (i) polyisocyanate, (ii) polyester polyol, (iii) blowing agent, and (iv) catalyst, the polyester polyol being preferably obtainable by reacting a dicarboxylic acid having from 4 to 8 carbon atoms with a dialcohol having from 2 to 6 carbon atoms and/or preferably having a weight-average molecular weight of from 500 to 4000 g/mol.

When using a first bandage material and a second bandage material having the features mentioned above under a) and b), it is possible to achieve a static sliding friction force $F_s$ of at least 3 N being required in order to move the first bandage material against the second bandage material in the wet state and a static sliding friction force $F_s$ of at least 6 N being required in order to move the first bandage material against the second bandage material in the dry state. When using materials other than those proposed here, it may be necessary to optimize the sliding friction force by varying the parameters mentioned above under a) and b). Experiments of this type can be carried out without relatively huge effort starting from the parameter ranges already proposed here.

Unless otherwise indicated in the relevant standards, all test methods are generally carried out at 23° C., 50% rel. air humidity and 1013 mbar pressure.

The invention comprises a therapeutic method for treating wound cavities on the human or animal body using the above-described composite (wound dressing) composed of first and second bandage material, the treatment being carried out in particular using negative pressure.

In an advantageous embodiment of the invention, a method for therapeutically treating wound cavities on the human or animal body by means of negative pressure is proposed, comprising i) providing a negative-pressure source, a suitable means for establishing communication of negative pressure between negative-pressure source and wound space (for example, a negative-pressure line and a negative-pressure connecting piece), a suitable means for sealing the wound space (for example, an airtight covering film) and also optionally a container for the aspirated wound fluids, ii) providing a first bandage material as wound contact layer, comprising a flexible, perforated film having a first and a second side, the perforations present in the film being introduced into the film in such a way that the perforation edges protrude from the second side of the film, with three-dimensional structures being present on the second side of the film, and the first side being intended for contacting with a wound base, more particularly the internal surface of a wound tube, iii) providing a second bandage material for introduction into a wound tube, comprising a porous polymer foam, the polymer foam being an open-cell polymer foam which comprises struts on or close to its surface and/or which comprises, on its surface, hollow spaces open toward the surface, and the struts and/or hollow spaces forming three-dimensional structures, iv) applying the second side of the film to the surface of the polymer foam immediately before the negative-pressure treatment, the polymer foam being partly or completely enveloped by the film, and the three-dimensional structures present on the surfaces of polymer foam and film forming an adhesive connection after contacting of polymer foam and film, v) introducing the composite composed of first and second bandage material into a wound cavity, it being possible to avoid as far as possible detachment of the film from the polymer foam during the process of introduction owing to the adhesive connection between the surfaces of polymer foam and film, vi) establishing airtight covering of the wound space and connection of a negative-pressure source, vii) and carrying out the negative-pressure therapy.

The adhesive connection of polymer foam and film established in step iv) shall avoid as far as possible detachment of the film from the polymer foam and/or movement of polymer foam and film while introducing, after step iv), the composite composed of first and second bandage material into a wound cavity. In this connection, it is advantageous when, after application of the second side of the film to the surface of the polymer foam, a static sliding friction force $F_s$ of at least 6 N, measured in accordance with DIN EN ISO 8235, is required in order to move the film in the dry state against the polymer foam in the dry state. This ensures an especially reliable adhesive connection of polymer foam and film.

Optionally, it is possible, after step v) and before the sealing of the wound space, to apply one or more further bandage plies, for example a further foam ply.

Typically, before the start of the negative-pressure therapy, i.e. even before step i), exploration of the wound, which may comprise probing of the cavity, is firstly carried out. Thereafter, the user can tailor both the perforated film and the porous polymer foam to the dimensions of the wound, for example by cutting to size. Optionally, the above-described method thus comprises, in step ii), tailoring of the film to the dimensions of the wound and/or, in step iii), tailoring of the polymer foam to the dimensions of the wound.

The application of the second side of the film to the surface of the polymer foam (step iv) is carried out immediately before placement of the wound dressing. In this connection, the term "application" comprises partial or complete envelopment of the foam by the film. Here, the film can optionally be wrapped in several turns around the second bandage material, and so the foam is partly or completely enveloped by more than one ply of film. Ideally, only one to three plies of the film should be placed on top of one another, since otherwise the permeability of the envelope for wound exudate lessens undesirably.

In a preferred embodiment for clinical practice, only one ply of the flexible film is applied as envelope to the foam.

In the case of a cylindrical foam block, it is optionally possible for only the sheath of the cylinder, which constitutes the substantial contact area with the wound base during the therapy, to be covered by the first film, whereas the cross-sectional areas of the cylinder remain uncovered. If the cross-sectional area pointing toward the negative-pressure source during use is not covered by the film, this can advantageously result in improved transfer of wound exudate to the negative-pressure source.

According to the invention, at least 75% of the surface of the second bandage material must be covered by the film, since otherwise there is the risk of granulation tissue adhesively bonding to and/or growing together with the foam. Preferably, at least 85% of the surface of the second bandage material is covered by the film, particularly preferably at least 95%. In a further particularly preferred embodiment, the total surface of the second bandage material is covered by the film.

It has been found that, surprisingly, the film does not necessarily have to be applied smoothly to the polymer foam. Instead, the surface of the film enveloping the polymer foam can by all means have folds or warps. Folds or warps can lead to the film being partially multilayered on the foam. Owing to the capillary effect already mentioned, sufficient draining of wound exudate can occur even in the regions in which folds or warps are present.

Advantageously, the polymer foam and the film can be removed in one step after completion of the negative-pressure therapy. This is possible in particular when the adhesive connection of polymer foam and film established in step iv) is present even in a wet state of the aforementioned components. To this end, the static sliding friction force $F_s$ required in order to move the film in the wet state against the polymer foam in the wet state should preferably be at least 3 N, measured in accordance with DIN EN ISO 8235. This ensures an especially reliable adhesive connection of polymer foam and film over the entire therapy.

In a further preferred embodiment, the bandage set comprises a polymer foam which contains embedded in its interior a drainage hose or another suitable conducting means. The hose can, for example, already be introduced by the manufacturer into the foam. It is also possible for the user, before application of the wound dressing, to introduce into the foam a continuous or blind-ending hole into which the drainage hose is then introduced. A drainage line present in the interior of the foam block can, if necessary, support the draining of wound exudate from the cavity and/or the maintenance of opening of the cavity during the application of negative pressure. An embodiment of this type could, for example, be used in the negative-pressure treatment of tubular cavities, more particularly continuous tunnel wounds, having a diameter of more than two centimeters.

In a further advantageous embodiment of the bandage set, at least one additional component which can further strengthen the adhesive connection between the first bandage material and the second bandage material can optionally be present on the first bandage material and/or on the second bandage material. The additional component can, for example, be an adhesive coating which is present on the second surface of the first bandage material and/or on the surface of the second bandage material. Preferably, the adhesive coating is applied to the second surface of the first bandage material, since coating of the surface of the second bandage material can go missing while tailoring the size of the foam. A further advantage of an adhesive coating applied to the second surface of the first bandage material is that the film regions which come to lie on top of one another during wrapping of the foam then likewise adhere to one another.

In the case of complex wounds, outwardly open wound regions which do not have any cavities and regions which have one or more wound cavities can be simultaneously present. For example, as a result of inflammatory processes, wound tubes may be present on the edge of a central, outwardly open wound region having an extended skin defect. Concerning this, it is proposed in the context of the present invention to treat the one or more cavities with the wound dressing according to the invention and to line the open regions with a porous bandage material, more particularly an open-cell polymer foam. However, it is also conceivable to likewise cover the outwardly open wound regions with the wound dressing according to the invention.

There is frequently also the need to treat wounds which have only a slight skin defect, but comprise multiple wound cavities of varying size. In the case of a wound of this type, a comparatively large wound pocket, for example at the center of the wound, to which one or more comparatively narrow wound tubes are connected may be present. In the context of the present invention, it can prove to be advantageous in such a situation to introduce the wound dressing according to the invention only into the narrow wound tubes, whereas the central pocket having larger dimensions is lined with a porous bandage material, more particularly an open-cell polymer foam.

In a further aspect of the invention, a product for use in the therapeutic treatment of wound cavities on the human or animal body by means of negative pressure is proposed. Here, the product is thus expressly claimed in connection with its specific medical use or indication, viz. the treatment of wound cavities. The product comprises i) a separately provided first bandage material as wound contact layer, comprising a flexible, perforated film having a first and a second side, the perforations present in the film being provided in such a way that the perforation edges protrude from the second side of the film, with three-dimensional structures being present on the second side of the film, and the first side being intended for contacting with a wound base, more particularly the internal surface of a wound tube, and ii) a separately provided second bandage material for introduction into a wound tube, comprising a porous polymer foam, the polymer foam being an open-cell polymer foam which comprises struts on or close to its surface and/or which comprises, on its surface, hollow spaces open toward the surface, and the struts and/or hollow spaces forming three-dimensional structures. The product is further notable for the fact that the structures present on the second side of the first bandage material can form an adhesive connection with the structures present on the surface of the second bandage material, and that the second side of the film is intended for partial or complete envelopment of the surface of the second bandage material immediately before the negative-pressure treatment, and so, after introduction of the composite composed of first and second bandage material into a wound cavity, movement of the first bandage material with respect to the second bandage material can be avoided as far as possible during the therapy and/or simultaneous removal of the first bandage material and the second bandage material is facilitated owing to the adhesive connection between the first bandage material and the second bandage material.

A further aspect in the context of the invention concerns a product for avoiding complications in the therapeutic treatment of wound cavities on the human or animal body by means of negative pressure. The complication is the retention of foam particles in the wound region, more particularly in a wound cavity. Here, the product is thus expressly claimed in connection with its specific medical use or indication, viz. avoiding a frequent and severe complication in the treatment of wound cavities. The product is the above-described product for use in the therapeutic treatment of wound cavities on the human or animal body by means of negative pressure.

Furthermore, the invention concerns a product for simplifying the therapeutic treatment of wound cavities on the human or animal body by means of negative pressure. Here, the product is thus expressly claimed in connection with its specific medical use, viz. simplifying the treatment of wound cavities. The product is the above-described product for use in the therapeutic treatment of wound cavities on the human or animal body by means of negative pressure.

In addition, the invention is directed to a flexible, perforated film as wound contact layer, for use in the treatment of wound cavities by means of negative pressure. Here, the film is expressly claimed in connection with its specific medical use, viz. use as wound contact layer in the negative-pressure treatment of wound cavities. Here, the film has a largely smooth first side intended for contacting with a wound base, more particularly the internal surface of a wound tube, and a rough second side. The perforations present in the film are provided in such a way that the perforation edges protrude from the second side of the film, with three-dimensional structures being present on the second side of the film. The three-dimensional structures can form an adhesive connection with three-dimensional structures present on a further bandage ply. The further bandage ply can be, in particular, an open-cell polymer foam suitable as wound filler.

In the context of the invention, a ready-to-use bandage set suitable for use in the therapeutic treatment of wound cavities on the human or animal body by means of negative pressure is likewise claimed, comprising a composite (wound dressing) according to any of the above-described embodiments, the first and the second bandage material both being in sterile form, and also optionally an airtight covering film for closing the wound space and/or a negative-pressure connecting piece. Here, the individual components should each be present in separate, sterile packaging, it being possible in turn to store the entirety of the components in a single outer packaging. Ideally, the sterilization is carried out after packaging of the components in the outer packaging, for example by using ethylene oxide.

Likewise encompassed by the invention is an apparatus suitable for use in the treatment of wound cavities by means of negative pressure, comprising a wound dressing according to any of the above-described embodiments, additionally comprising an airtight covering film, a negative-pressure connecting piece, a negative-pressure line, a negative-pressure source and also optionally a container for the aspirated wound fluids.

Use Example I

Bullet wound on the upper arm (perforating wound) having a continuous tubular cavity.

After exploration of the wound, debridement is firstly carried out. To treat the tubular wound cavity, the physician performing the treatment tightly wraps a microperforated polyethylene film (width of the film web: 3 cm) around a cuboidal foam block (having sides a; b; c, the length of a being 2 cm for example, of b being 2 cm for example and of c being 7 cm for example) tailored to the size of the wound tube. About three turns are applied in an offset manner, and so the foam contains two film plies in the overlapping region and one film ply in each case outside the overlapping region. The two side areas (a; b and oppositely a'; b') are not covered by film, and so, in said exemplary case, about 88% of the foam surface is covered by a film. A suitable foam is, for example, the commercially available product VivanoMed® Foam (Paul Hartmann AG, Germany), an open-cell polymer foam composed of polyester polyurethane. The polyethylene film preferably comprises about 270 to 290 perforations per $cm^2$ area of film, each with a diameter of 0.3 mm. The perforations are preferably present in the film in such a way that the perforation edges protrude from the surface of the film. Thus, a crater-shaped, three-dimensional structure is present on one surface of the film, whereas the other opposing surface of the film is largely smooth. The open area of the film is preferably from 20% to 22%. When wrapping the foam, the film is wrapped with its rough side (protruding perforation edges) on the foam. Here, the film adheres to the foam. The wound dressing which is prepared in this manner and which, after wrapping, has an altogether tubular shape is introduced into the wound tunnel through the opening present on the exit wound site. The ends of the wound dressing should, on both sides of the wound channel, preferably be situated about 1 to 2 cm below the plane of the undamaged wound surroundings. A trimmed foam block (VivanoMed® Foam) is applied to both ends of the wound dressing such that the entry wound site and the typically larger exit wound site are completely filled with the foam up to the plane of the undamaged wound surroundings. A transparent self-adhesive film bandage (Hydrofilm®, Paul Hartmann AG, Germany) is applied to the foam on both the entry wound site and the exit wound site for airtight covering of the wound and fixed on the undamaged skin surrounding the wound. Subsequently, into one of the negative-pressure bandages present on both sides of the wound channel, a hole is cut into the film bandage. The hole is preferably introduced into the transparent film bandage situated over the exit wound site. A negative-pressure connecting piece (for example, a VivanoTec® Port, Paul Hartmann AG, Germany) is fixed in a sealing manner over the hole. The negative-pressure connecting piece can then be connected via a secretion line to a negative-pressure therapy unit (VivanoTec®, Paul Hartmann AG, Germany). The negative-pressure therapy unit preferably comprises an interchangeable secretion container, for example one having a capacity of 850 ml. Subsequently, a constant negative pressure of 125 mmHg is applied for a period of two days. After preferably two days, the bandage is changed and the wound assessed. Owing to the adhesion between film and foam, the enveloped foam body introduced into the wound channel can be removed easily and in one piece.

The treatment is, as described above, repeated until sufficient granulation tissue is present and the wound tube has become overgrown. Before placement of a new negative-pressure bandage, debridement is normally repeated.

After sufficient granulation tissue has formed and the wound tunnel has closed, the patient can, for example, be prepared for a split skin graft or further treated with conventional wound products. For the split skin graft, a thin skin layer is taken from another site of the patient's body. In the case of a split skin graft, the wound can be advantageously treated again by means of negative-pressure therapy. Methods for treating a transplantation wound of this type by means of negative pressure are known from the prior art.

Use Example II

Complex decubitus wound having a central, large-area and outwardly open wound hollow and a tubular wound pocket branching from the side, the wound pocket being blind-ending.

After exploration of the wound, debridement is firstly carried out, as in use example I. The dimensions of the subcutaneous wound channel are estimated by probing. To treat the tubular subcutaneous wound region, the physician performing the treatment tightly wraps, analogously to use example I, a microperforated polyethylene film around a cuboidal foam block of suitable size that is tailored to the size of the wound tube. The wound dressing which is prepared in this manner and which has, after wrapping, an altogether tubular shape is fully introduced into the blind-ending wound channel. Owing to the adhesion between film and foam, the foam envelopment immediately applied before the treatment remains intact while the wound dressing is introduced into the cavity. The central, open region of the wound is covered by a foam block (VivanoMed® Foam) tailored to the wound shape by cutting to size. Preferably, the wound base may be covered by a suitable wound contact layer (for example, Atrauman Ag®, Paul Hartmann AG, Germany) in the open region of the wound before application of the foam. The entire wound region is covered by a transparent, self-adhesive film bandage (Hydrofilm®, Paul Hartmann AG, Germany) for airtight sealing of the wound. The film bandage is fixed on the intact skin surrounding the wound. A hole is introduced into the film bandage. As in use example I, a negative-pressure connecting piece (for example, a VivanoTec® Port, Paul Hartmann AG, Germany) is fixed in a sealing manner over the hole. The negative-pressure connecting piece can then be connected via a secretion line to a negative-pressure therapy unit (VivanoTec®, Paul Hartmann AG, Germany). Subsequently, constant or variable negative pressure, for example in the range from 80 to 125 mmHg, is applied for a period of preferably one to three days. Since the adhesion between film and foam is also preserved during the therapy, the enveloped foam body introduced into the subcutaneous wound channel can be removed easily and in one piece during the bandage change following the negative-pressure therapy. The envelopment prevents, as far as possible, foam particles from being able to remain in the wound cavity.

The treatment can be repeated until sufficient granulation tissue is present in the wound channel and the wound tube has become overgrown. Before placement of a new negative-pressure bandage, debridement is normally repeated. To treat the open wound region, the negative-pressure therapy can be continued using customary bandage components known from the prior art until the wound has healed.

Determination of Sliding Friction Force $F_s$

The static sliding friction force $F_s$ of a film surface against a foam surface was determined analogously to DIN EN ISO 8295 (October 2004 edition) using the test instrument described in the standard (tensile test machine from Zwick, Germany), with a level test table being used. Three samples were measured in each case and the mean was calculated from the three measurements. For measurement of the samples in the dry state, conditioning was carried out before the test for at least 16 h in a standard atmosphere at 23° C., 50% relative air humidity, 1013 mbar. For measurement of the samples in the wet state, the samples (foam and film)

were completely immersed in water. Thereafter, the samples were held vertically for 30 s to allow dripping and clamped into the test instrument. The foam ply (dimensions 150×300 mm) was fixed on the test table, whereas the film ply (dimensions 65×200 mm) was clamped into the sled. The period between dripping and the start of measurement was no greater than 2 min. The square contact footprint of the sled covered with the film was 40 cm². The sled was drawn across the immobile test table. The test speed was 100 mm/min. The weight of the traction sled including the friction block was 200 g. The prestress between sled and force measurement instrument was 0.2 N.

Example: Determination of the Sliding Friction Force of a First Bandage Ply Against a Second Bandage Ply on a Test Instrument The static sliding friction force $F_s$ was determined, as described above, analogously to DIN EN ISO 8295.

Sample pair 1—Open-cell foam against a slit film having a largely smooth surface.

Foam: Hydrophobic polyester polyurethane foam. Bulk density as per ISO 845 of 25.8 kg/m³, compressive strength as per DIN EN ISO 3386-1 of 3.9 kPa, tensile strength as per DIN 53571 A of 170 kPa, elongation at break as per DIN 53571 A of 290%, cell count (determined microscopically on a straight line laid out on the surface of the foam) of 11/cm, air permeability as per DIN EN ISO 9237 of 2680 l/m²s. A foam of this type that is usable as wound dressing is commercially available under the name VivanoMed® Foam (Paul Hartmann AG, Germany).

Film: Smooth, transparent polyurethane film having slits. Approximately 20 slits distributed across the surface of the film, each slit 4.5 mm in length, were introduced into the film per 100 cm² of film surface. The slits were aligned in parallel to the machine direction (MD) of the film. When using a film of this type as wound contact layer or organ-protecting layer, the slits serve to conduct wound exudate. The use of slitted films as wound contact layer, especially in the context of negative-pressure therapy, is known from the prior art.

The film was clamped into the measurement sled in such a way that the sled moved along the machine direction of the film.

Sample pair 2—Open-cell foam against a slit film comprising a three-dimensional crater-shaped structure on one surface.

Foam: Hydrophobic polyester polyurethane foam. Bulk density as per ISO 845 of 25.8 kg/m³, compressive strength as per DIN EN ISO 3386-1 of 3.9 kPa, tensile strength as per DIN 53571 A of 170 kPa, elongation at break as per DIN 53571 A of 290%, cell count (determined microscopically on a straight line laid out on the surface of the foam) of 11/cm, air permeability as per DIN EN ISO 9237 of 2680 l/m²s. A foam of this type that is usable as wound dressing is commercially available under the name VivanoMed® Foam (Paul Hartmann AG, Germany).

Film: Transparent polyethylene film rough on one side and having perforations. The film comprises about 280 perforations per cm² of film surface, each perforation having a diameter of 0.3 mm. The perforations were introduced into the film in such a way that the perforation edges protrude from the second surface of the film, and so a crater-shaped, three-dimensional structure is present on the second surface. By contrast, the first surface of the film is largely smooth. The open surface area of the film is 21%. The film was clamped into the measurement sled in such a way that the sled moved along the machine direction (MD) of the film. The rough side of the film (second surface) was aligned toward the test table, and so the rough side was in contact with the foam.

The static sliding friction force present between the material plies (sample pairs) was determined in each case for dry and wet samples by means of the measurement method specified above. The mean values of the measured sliding friction force $F_s$ from three measurements in each case are reported below.

| | |
|---|---|
| Sample pair 1 - dry | 0.98 N |
| Sample pair 1 - wet | 0.72 N |
| Sample pair 2 - dry | 10.08 N |
| Sample pair 2 - wet | 5.86 N |

REFERENCE SIGNS

1 Negative-pressure source
2 Secretion container (canister for wound exudate)
3 Wound base
5 Wound edge
6 Airtight covering film for closing the wound space
7 Negative-pressure connecting means (port)
8 Negative-pressure line
9 Opening in covering film
10 Foam partly enveloped by a perforated film
11, 21, 31 Perforated, flexible film (wound contact layer)
12, 22, 32, 35 Open-cell polymer foam
13 Hollow space in the open-cell polymer foam that is open toward the surface
14 Foam strut present on or close to the first surface of the open-cell polymer foam
15 Perforation in the flexible film
16 Perforation edge in the flexible film. The perforation edge protrudes from the second surface of the film, forming a three-dimensional structure on the second surface of the film
20, 30 Apparatus, applied to a wound, for the therapeutic treatment of wound cavities by means of negative pressure
25 First wound site
26 Second wound site
24 Continuous wound tube (tunnel wound)
33 Central, outwardly open wound cavity
34 Blind-ending wound tube (wound pocket)

FIGURES

The bandage set according to the invention or the use of the bandage set in the context of an apparatus for negative-pressure wound therapy will now be more particularly elucidated with reference to diagrammatic drawings (not true to scale). However, the invention is not to be understood to be reduced to the embodiments depicted in the drawings or in the description of the drawing. On the contrary, the invention also encompasses combinations of the individual features of the alternative forms.

FIG. 1b shows a micrograph (REM) of an open-cell polymer foam suitable as second bandage material, in plan view. The micrograph therefore shows surface detail (original size 6 mm×6 mm) of bandage material 12 from FIG. 1a.

Figure 1A:
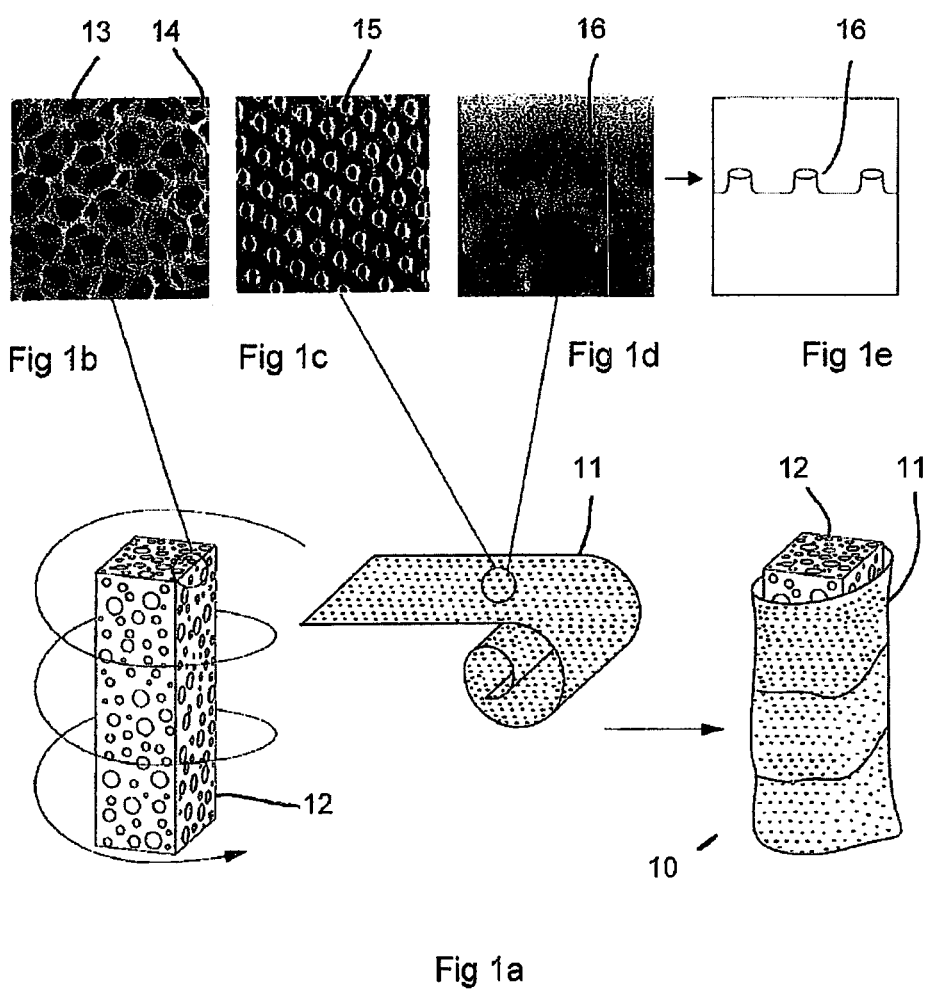
FIG. 1a shows a diagram of a preferred embodiment of the invention.

FIGS. 1c/d show a micrograph (reflected-light microscope) of a perforated film suitable as first bandage material, in plan view of the second side (FIG. 1c; original size approximately 23 mm×23 mm) and from the side (FIG. 1d; original size approximately 9 mm×9 mm). The micrographs therefore show a surface detail present on the second side of ply 11 from FIG. 1a.

FIG. 1e shows a diagram of the surface detail from FIG. 1d.

Figure 2:
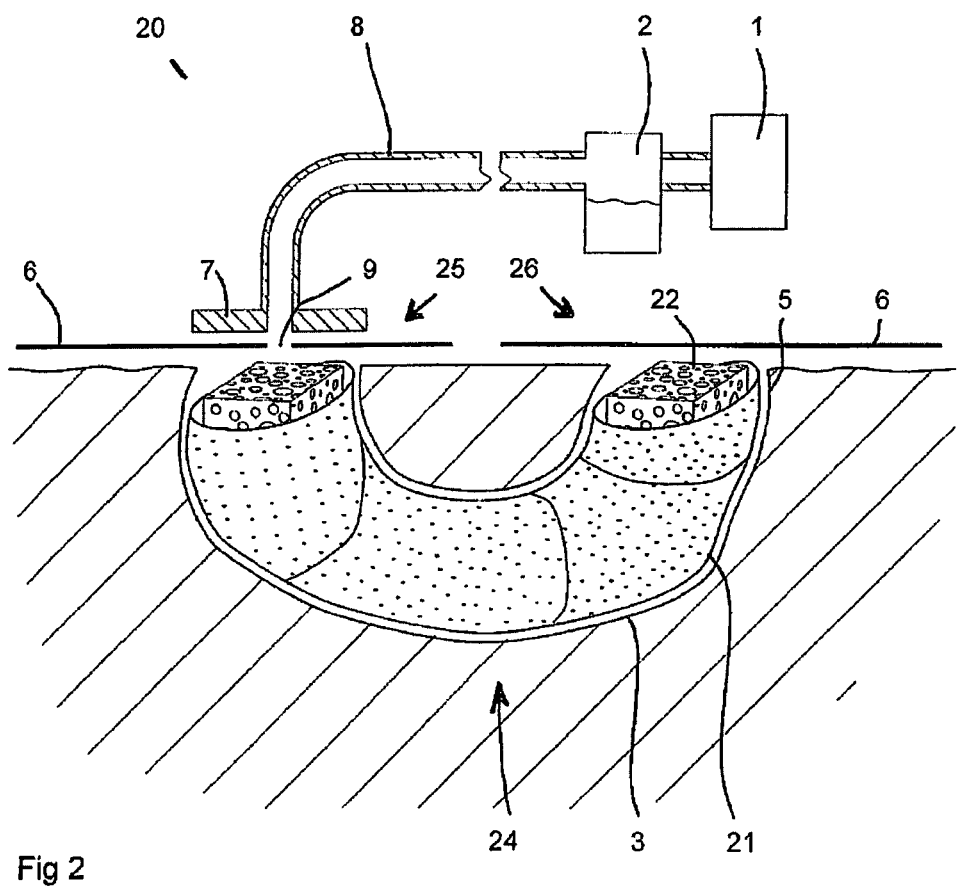

FIG. 2 shows a diagram of a negative-pressure bandage placed on a tunnel-type wound cavity.

Figure 3:
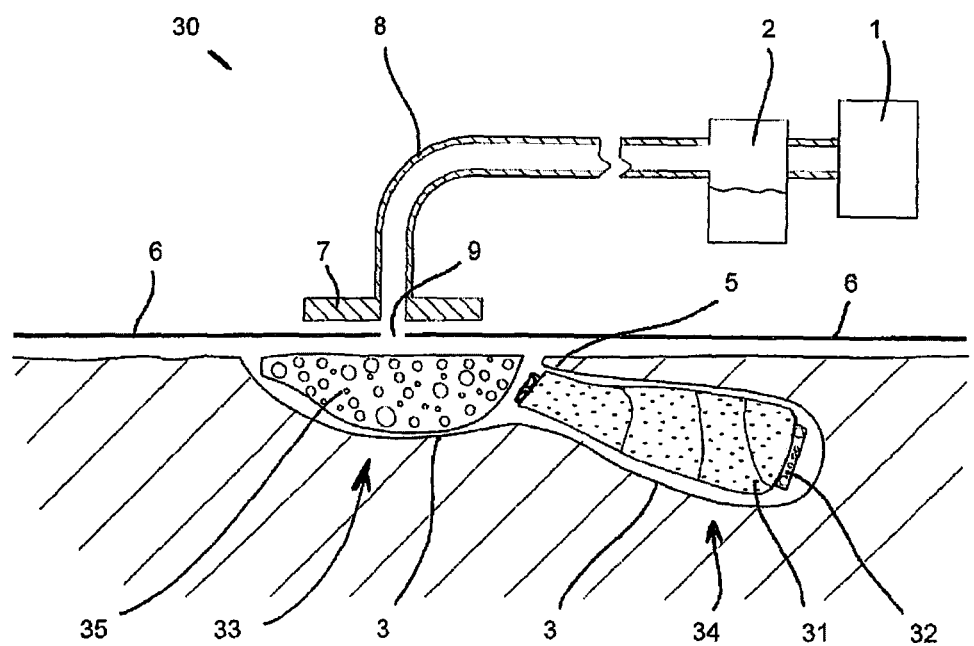

FIG. 3 shows a diagram of a negative-pressure bandage placed on a wound, the wound comprising a blind-ending cavity.

FIG. 1a depicts, by way of example, a preferred embodiment of the bandage set (10) according to the invention, which comprises, as wound contact layer, a first bandage material (11) provided separately before use and, as wound filler, a second bandage material (12, 22) in cuboidal form in the present example, it being possible for the first and the second bandage material to adhere to one another owing to its three-dimensional structures present on the surfaces. The wound filler (second bandage material 12, 22) can therefore be enveloped with a wound contact layer (first bandage material 11, 21) immediately before use by the physician without additional aids, the composite being maintained over the entire period of the therapy including the removal of the wound dressing after the treatment. The left-hand side of FIG. 1a depicts the separately provided first and second bandage material, whereas the right-hand side depicts a foam (second bandage material) enveloped by the film (first bandage material). To this end, the film (11) was wrapped in about three turns around the cuboidal foam block (12). Because the surfaces of film (11) and foam (12) adhere to one another, further fixing of the film (11) to the foam (12) is not necessary. The upper and the lower (not visible in FIG. 1a) lateral surface of the foam block (12) was not covered with film in the example depicted in FIG. 1a. Nevertheless, the foam block can also be completely enveloped by the film (11) (not depicted). The film (11) serving to envelop the foam (12) and serving as wound contact layer can be applied in any desired manner to the foam, for example by wrapping or by laying on individually trimmed film sections. Preferably, a single strip-shaped film web is applied. It is essential that at least 75% of the surface of the foam block (12), preferably at least 85% of the surface, in particular at least 95% of the surface, is covered by the film (11). According to the invention, the first bandage material comprises a flexible, perforated film, whereas the second bandage material comprises a porous polymer foam. The flexible film (11) comprises, on its second side, a multiplicity of three-dimensional perforations distributed across the surface of the film. The film (11) therefore has a smooth first side and a roughened second side owing to the perforations (15) introduced into the film. FIGS. 1c and 1d show micrographs of a perforated polyethylene film (11) suitable for the embodiment depicted here, in plan view of the second side (FIG. 1d) and from the side (FIG. 1d). FIG. 1e shows a diagram of the surface detail from FIG. 1d. It can be seen from FIGS. 1c, 1d and 1e that there are microstructures (16) which protrude as craters from the plane of the film and which give the second surface of the film (11) a rough surface quality. The crater-type structures (16), which are approximately 400 μm in height (maximum extent of the three-dimensional structure, measured perpendicularly with respect to the plane of the film), are perforation edges. In the interior of the microstructures (16), there are openings or channels (15) which penetrate the film. The diameter of the openings is, in each case, approximately 0.3 mm. The film shown in FIGS. 1a and 1c has an open surface of 21%, making it possible to ensure effective draining of the wound exudates released in a wound cavity during the therapy. FIGS. 1c and 1d therefore show a detail of the second surface of the flexible film (11) depicted only diagrammatically in FIG. 1a. FIG. 1b shows a micrograph of the surface of the open-cell polymer foam (12). In the photograph (FIG. 1b), foam struts (14) and hollow spaces (13) can be seen. The foam struts (14) and the hollow spaces (13) form on the foam surface a three-dimensional microstructure which can form an adhesive connection with the crater-shaped microstructures (16) present on the second side of the flexible film (11), when the second surface of the film (11) is contacted with the first surface of the foam (12). The porous polymer foam is preferably an open-cell foam composed of polyurethane or polyvinyl alcohol (PVA), more particularly polyester polyurethane. The outer shape of the foam block can be tailored by the user to the wound cavity to be treated. Preferably, the foam block is present in the form of a hose-shaped cylinder or in the form of a cuboid.

FIG. 2 shows the use of a composite composed of first and second bandage material in the treatment of a tunnel-type wound cavity (24) by means of negative pressure. The hose-shaped foam block (22) at least partly enveloped by a film (21) was completely introduced into the wound tube (24). Here, the film (21) acts as a wound contact layer which is in immediate contact with the wound base (3), i.e. with the walls of the cavity. The wound sites (25, 26) on the exit openings of the cavity (24) are sealed in a negative-pressure-tight manner with an air-impermeable covering film (6), for example a transparent film bandage, the covering film (6) being adhesively fixed in the wound surroundings on the intact skin. Preferably, the covering film (6) used for sealing the negative-pressure bandage is a polyurethane film coated with self-adhesive, for example the commercially available product Hydrofilm® (Paul Hartmann AG, Germany). An opening (9) having a diameter of approximately 0.5 cm is introduced into the covering film (6) at the first sealed wound site (25), i.e. at a first exit site of the tunnel-shaped cavity. A negative-pressure connecting means (port, 7), which is connected to a negative-pressure line (8), is fixed over the opening (9), making it possible to establish communication of negative pressure between the lumen of the negative-pressure line (8) and the wound space. After activation of the negative-pressure source (1), negative pressure can be established in the wound space and wound secretions can be sucked into the container (2). It would also be conceivable to apply, in each case, a negative-pressure connecting piece to both wound sites (25, 26), making it possible to apply negative pressure to the continuous tubular wound cavity (24) at both sides. A further variant of negative-pressure application not depicted in FIG. 2 consists in applying a negative-pressure connecting piece to the first wound site (25), whereas a small opening is introduced into the covering film at the second wound site (26) (not depicted in FIG. 2). During application of negative pressure, it is thus possible to generate a directed fluid stream through the wound tube (24) toward the negative-pressure connecting piece (7). Here, the opening should be provided in such a way that only a slight amount of air can enter the wound space (cavity 24). Preferably, the air enters here across a filter (not depicted in FIG. 2) arranged over the opening, and so only sterile external air can reach the wound space. In a further advantageous embodiment, a valve allowing specific regulation of the entry of air is additionally attached in addition to the filter over the opening. While the valve is closed, the wound space can communicate only across the negative-pressure connecting piece. The negative pressure in the wound space then largely matches the negative pressure provided by the pump. After opening of the valve, a slight amount of external air can enter the wound cavity across an opening of the tunnel tube. The air is then guided through the wound tube in the interior of the composite composed of first and second bandage material and escapes across the negative-pressure connecting piece. Such flushing of the cavity with external air can promote the draining of wound exudate, the flushing with air preferably being effected only temporarily in order to avoid excessive drying-up of the wound base (3) in the cavity, for example by opening the valve several times during the day (for example, three times per day) for a few minutes (for example, 5 min) and then closing it again.

FIG. 3 shows the use of a composite composed of first and second bandage material in the treatment of a blind-ending, pocket-shaped wound cavity (34) by means of negative pressure. In the example shown in FIG. 3, there is an outwardly open wound region (33), from the lateral wall of which the wound channel (34) branches off. The hose-shaped foam block (32) at least partly enveloped by a film (31) is introduced into the cavity (34), i.e. into the undermined, subdermal region of the wound space. Here, it is advantageous when the end portion of the composite composed of foam film projects slightly, for example from 0.5 to 2 cm, into the open wound region (33), and so the wound pocket (34) is kept open during the application of negative pressure by the enveloped foam. Here, the perforated film (31) acts as a wound contact layer which is in immediate contact with the wound base (3), i.e. the walls of the cavity. The surface of the foam block (32) pointing to the outwardly open wound region (33) is preferably free, i.e. not covered with the film (31). A further porous polymer foam (35) which is not enveloped by a film and which is tailored to the size and extent of the open wound region (33) is introduced into the outwardly open wound region (33). The lateral surface of the foam block (32) enveloped by film (31) should if possible be in direct contact with the further polymer foam (35) in order to ensure efficient draining of wound exudate aspirated from the cavity (34). If necessary, a wound contact layer (not depicted in FIG. 3) can be inserted between the further polymer foam (35) and the wound base. The wound contact layer used can, for example, likewise be a perforated film. Alternatively, use can be made of bandage material known from the prior art and suitable for use as wound contact layer, for example ointment dressings, more particularly ointment dressings containing an antimicrobial substance. An ointment dressing suitable as wound contact layer in the context of the present invention is the commercially available product Atrauman Ag® (Paul Hartmann AG, Germany). The wound site is, as described in FIG. 2, sealed in a negative-pressure-tight manner with an air-impermeable covering film (6), for example a transparent film bandage, the covering film (6) being adhesively fixed in the wound surroundings on the intact skin. An opening (9) having a diameter of approximately 0.5 cm is introduced into the covering film (6). A negative-pressure connecting means (port, 7), which is connected to a negative-pressure line (8), is fixed over the opening (9), making it possible to establish communication of negative pressure between the lumen of the negative-pressure line (8) and the wound space. After activation of the negative-pressure source (1), negative pressure can be established in the wound space and wound secretions can be sucked into the container (2). In a further embodiment not depicted in FIG. 3, it would be possible to introduce a drainage line into the interior of the foam block before application of the wound dressing.

The invention claimed is:

1. A bandage set suitable for use in negative-pressure treatment of wound cavities comprising
   i) a first bandage material as wound contact layer, comprising a flexible, perforated film (11, 21, 31) having a first and a second side, and having perforations (15) present in the flexible, perforated film being provided in such a way that the perforation edges (16) protrude from solely the second side of the flexible, perforated film (11, 21, 31), which perforation edges form three-dimensional structures solely on the second side of the flexible, perforated film (11, 21, 31), wherein the three-dimensional structures present solely on the second side of the flexible perforated film (11, 21, 31) are in the form of crater-shaped structures, and the first side, which is smooth, being intended for contacting with a wound base (3),
   ii) a separately provided second bandage material for introduction into a wound cavity, comprising a porous polymer foam (12, 22, 32), the porous polymer foam (12, 22, 32) being an open-cell porous polymer foam with a surface which open-cell polymer foam (12, 22, 32) comprises struts (14) on or close to the surface of the open-cell polymer foam and which comprises, on the surface of the open-cell polymer foam, hollow spaces (13) open toward the surface of the open-cell polymer foam, and wherein the hollow spaces (13) open toward the surface are cells which are present in the interior of the open-cell polymer foam (12, 22, 32) and which are exposed and become the hollow spaces (13) open towards the surface by a cutting of the foam during the production of the second bandage material wherein the interior of the foam contains an intact cell structure which is not exposed by the cutting of the foam during the production of the second bandage material, and where the struts (14) and hollow spaces (13) form three-dimensional structures on the surface of the open-cell polymer foam, characterized in that
   the first bandage material has a surface area sufficient to envelop at least 75% of the surface of the second bandage material,
   and the three-dimensional structures present on solely the second side of the flexible, perforated film (11, 21, 31) form an adhesive connection with the three-dimensional structures present on the surface of the open-cell porous polymer foam by having the crater-shaped structures on the second side of the flexible perforated film (11, 21, 31) penetrate the hollow spaces (13) of the three-dimensional structures on the surface of the open-cell polymer foam to form a form-fit and/or force-fit adhesive connection,
   the second side of the flexible, perforated film (11, 21, 31) being intended for partial or complete envelopment of the surface of the porous polymer foam (12, 22, 32) immediately before treatment of a wound cavity, and wherein the bandage set is such that after introduction of the bandage set composed of first and second bandage material into a wound cavity, movement of the first bandage material with respect to the second bandage material is prevented during the negative pressure treatment and/or simultaneous removal of the first bandage material and the second bandage material is facilitated owing to the adhesive connection between the first bandage material and the second bandage material.

2. The bandage set according to claim 1, wherein a static sliding friction force $F_s$, measured in accordance with DIN EN ISO 8235, of at least 3 N is required in order to move the first bandage material in the wet state against the second bandage material in the wet state and/or wherein a static sliding friction force $F_s$ of at least 6 N, measured in accordance with DIN EN ISO 8235, is required in order to move the first bandage material in the dry state against the second bandage material in the dry state.

3. The bandage set according to claim 1, wherein the surface area of the first side of the first bandage material is at least 80% and not more than 5000%, of the surface of the open-cell porous polymer foam.

4. The bandage set according to claim 1, wherein the second bandage material is present in the form of a hose-shaped cylinder, the height (h) of which is at least three times, in particular at least five times, the diameter.

5. The bandage set according to claim 1, wherein the second bandage material is present in the form of a cuboid stretched in length and having sides (a; b; c), the cuboid having a ratio of the side lengths of the cross-sectional area formed by sides (a; b) of 0.5<(a:b)<2, and wherein the longer side c is greater than the diagonal of the cross-sectional area.

6. The bandage set according to claim 1, wherein the perforations (15) present in the flexible, perforated film (11, 21, 31) have an open diameter of at least 0.2 mm and not more than 0.4 mm.

7. The bandage set according to claim 1, wherein the second bandage material comprises a drainage hose introduced into the interior of the porous polymer foam (12, 22, 32), making it possible to apply negative pressure to the porous foam (12, 22, 32) and to transport fluids out of the porous foam (12, 22, 32) toward a negative-pressure source (1).

8. The bandage set according to claim 1, wherein at least one additional component which can further strengthen the adhesive connection between the first bandage material and the second bandage material is present on the first bandage material and/or on the second bandage material.

9. The bandage set according to claim 8, wherein the additional component is an adhesive coating.

10. The bandage set according to claim 1, wherein the first and the second bandage material are both individually available off-the-shelf and in sterile form.

11. The bandage set according to claim 10, further comprising an airtight covering film (6) for airtight sealing of the wound area and optionally a negative-pressure connecting piece (7) for applying negative pressure to the wound space.

12. A composite composed of at least two components, suitable for use in negative pressure treatment of wound cavities, comprising
   i) a first bandage material as wound contact layer, comprising a flexible, perforated film (11, 21, 31) having a first and a second side, and having perforations (15) present in the flexible, perforated film (11, 21, 31) being provided in such a way that the perforation edges (16) protrude solely from the second side of the flexible, perforated film (11, 21, 31), which perforation edges form three-dimensional structures solely on the second side of the flexible, perforated film (11, 21, 31), wherein the three-dimensional structures on the second side of the flexible perforated film (11, 21, 31) are in the form of cater-shaped structures, and the first side, which is smooth being intended for contacting with a wound base (3),
   ii) a second bandage material for introduction into a wound cavity, comprising a porous polymer foam (12, 22, 32), the porous polymer foam (12, 22, 32) being an open-cell porous polymer foam with a surface which comprises struts (14) on or close to the surface of the open-cell polymer foam and which comprises, on the surface of the open-cell polymer foam, hollow spaces (13) open toward the surface of the open-cell polymer foam, and wherein the hollow spaces (13) open toward the surface are cells which are present in the interior of the open-cell polymer foam (12, 22, 32) and which are exposed and become the hollow spaces (13) open towards the surface by a cutting of the foam during the production of the second bandage material wherein the interior of the foam contains an intact cell structure which is not exposed by the cutting of the foam during the production of the second bandage material, and where the struts (14) and hollow spaces (13) form three-dimensional structures on the surface of the open-cell polymer foam,
characterized in that
   the three-dimensional structures present on solely the second side of the flexible perforated film (11, 21, 31) form an adhesive connection with the three-dimensional structures present on the surface of the open-cell porous polymer foam by having the crater-shaped structures on the second side of the flexible perforated film (11, 21, 31) penetrate the hollow spaces (13) of the three-dimensional structures on the surface of the open-cell polymer foam to form a form-fit and/or force-fit adhesive connection,
   and the flexible, perforated film (11, 21, 31) is present on at least 75% of the surface of the porous polymer foam (12, 22, 32) and thus forms an envelopment of the porous polymer foam (12, 22, 32), the flexible, perforated film (11, 21, 31), with its second side, being in contact with the porous polymer foam (12, 22, 32),
   and wherein the composite is such that after introduction of the composite composed of first and second bandage material into a wound cavity, movement of the first bandage material with respect to the second bandage material is prevented during the negative pressure treatment and/or simultaneous removal of the first bandage material and the second bandage material is facilitated owing to the adhesive connection between the first bandage material and the second bandage material.

13. An apparatus suitable for use in negative pressure treatment of wound cavities comprising a bandage set according to claim 1, an airtight covering film (6), a negative-pressure connecting piece (7), a negative-pressure line (8), a negative-pressure source (1) and also optionally a container (2) for the aspirated wound fluids.

14. A product for use in negative pressure treatment of wound cavities comprising
   i) a first bandage material as wound contact layer, comprising a flexible, perforated film (11, 21, 31) having a first and a second side, and having perforations present in the flexible, perforated film (11, 21, 31) being provided in such a way that the perforation edges (16) protrude from solely the second side of the flexible, perforated film (11, 21, 31), which perforation edges form three-dimensional structures solely on the second side of the flexible, perforated film (11, 21, 31), wherein the three-dimensional structures solely on the second side of the flexible perforated film (11, 21, 31) are in the form of crater-shaped structures, and the first side being smooth, and being intended for contacting with a wound base, ii) a separately provided second bandage material for introduction into a wound cavity, comprising a porous polymer foam (12, 22, 32), the porous polymer foam (12, 22, 32) being an open-cell polymer foam which comprises struts (14) on or close to the surface of the open-cell polymer foam and which comprises, on the surface of the open-cell polymer foam, hollow spaces (13) open toward the surface of the open-cell polymer foam, and wherein the hollow spaces (13) open toward the surface are cells which are present in the interior of the open-cell polymer foam (12, 22, 32) and which are exposed and become the hollow spaces (13) open towards the surface by a cutting of the foam during the production of the second bandage material wherein the interior of the foam contains an intact cell structure which is not exposed by the cutting of the foam during the production of the second bandage material, and where the struts (14) and hollow spaces (13) form three-dimensional structures on the surface of the open-cell polymer foam, characterized in that the three-dimensional structures present solely on the second side of the flexible, perforated film (11, 21, 31) form an adhesive connection with the three-dimensional structures present on the surface of the open-cell polymer foam, by having the crater-shaped structures on the second side of the flexible perforated film (11, 21, 31) penetrate the hollow spaces (13) of the three-dimensional structures on the surface of the open-cell polymer foam to form a form-fit and/or force-fit adhesive connection, the second side of the flexible, perforated film (11, 21, 31) being intended for partial or complete envelopment of the surface of the porous polymer foam (12, 22, 32) immediately before treatment of a wound cavity, and wherein the product is such that after introduction of the product composed of first and second bandage material into a wound cavity, movement of the first bandage material with respect to the second bandage material is prevented during the negative pressure treatment and/or simultaneous removal of the first bandage material and the second bandage material is facilitated owing to the adhesive connection between the first bandage material and the second bandage material.

15. A method for negative pressure treatment of wound cavities comprising providing a negative-pressure source (1) and also optionally a container (2) for the aspirated wound fluids, providing a negative pressure connecting port (7) which is connected to a negative pressure connecting line (8) in order to establish communication of negative pressure between negative-pressure source (1) and wound space, providing an air-tight covering film for sealing the wound space, providing a first bandage material as wound contact layer, comprising a flexible, perforated film (11, 21, 31) having a first and a second side, and having perforations (15) present in the flexible, perforated film (11, 21, 31) being provided in such a way that the perforation edges (16) protrude from solely the second side of the flexible, perforated film (11, 21, 31), which perforation edges form three-dimensional structures solely on the second side of the flexible, perforated film (11, 21, 31), wherein the three-dimensional structures solely on the second side of the flexible perforated film (11, 21, 31) are in the form of crater-shaped structures, and the first side which is smooth, being intended for contacting with a wound base (3), providing a second bandage material for introduction into a wound tube, comprising a porous polymer foam (12, 22, 32), the porous polymer foam (12, 22, 32) being an open-cell polymer foam which comprises struts (14) on or close to the surface of the open-cell polymer foam and which comprises, on the surface of the open-cell polymer foam, hollow spaces (13) open toward the surface of the open-cell polymer foam, and wherein the hollow spaces (13) open toward the surface are cells which are present in the interior of the open-cell polymer foam (12, 22, 32) and which are exposed and become the hollow spaces (13) open towards the surface by a cutting of the foam during the production of the second bandage material wherein the interior of the foam contains an intact cell structure which is not exposed by the cutting of the foam during the production of the second bandage material, and the struts (14) and hollow spaces (13) forming three-dimensional structures on the surface of the open-cell polymer foam, applying the second side of the flexible, perforated film (11, 21, 31) to the surface of the polymer foam (12, 22, 32) immediately before treatment of a wound cavity, the porous polymer foam (12, 22, 32) being partly or completely enveloped by the flexible, perforated film (11, 21, 31), and the three-dimensional structures present on the surfaces of porous polymer foam (12, 22, 32) and flexible, perforated film (11, 21, 31) forming an adhesive connection after contacting of porous polymer foam (12, 22, 32) and film (11, 21, 31), by having the crater-shaped structures on the second side of the flexible perforated film (11, 21, 31) penetrate the hollow spaces (13) of the three-dimensional structures on the surface of the open-cell polymer foam to form a form-fit and/or force-fit adhesive connection, introducing a composite composed of first and second bandage material into a wound cavity, detachment of the flexible, perforated film (11, 21, 31) from the porous polymer foam (12, 22, 32) being prevented during the process of introduction owing to the adhesive connection between the surfaces of porous polymer foam (12, 22, 32) and flexible, perforated film (11, 21, 31), optionally applying further bandage plies, establishing airtight covering of the wound space and connection of the negative-pressure source (1), carrying out the negative-pressure treatment, and optionally simultaneously removing porous polymer foam (12, 22, 32) and flexible, perforated film (11, 21, 31) in one step after completion of the negative-pressure treatment.

16. The method according to claim 15, wherein, after application of the second side of the flexible, perforated film (11, 21, 31) to the surface of the porous polymer foam (12, 22, 32), a static sliding friction force $F_s$ of at least 6 N, measured in accordance with DIN EN ISO 8235, is required in order to move the flexible, perforated film (11, 21, 31) in the dry state against the porous polymer foam (12, 22, 32) in the dry state.

* * * * *